United States Patent
Lajtai

(10) Patent No.: US 6,613,065 B2
(45) Date of Patent: *Sep. 2, 2003

(54) DEVICE FOR GUIDING A MEDICAL INSTRUMENT

(75) Inventor: Georg Lajtai, Wels (AT)

(73) Assignee: Karl Storz GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 87 days.

(21) Appl. No.: 09/797,009

(22) Filed: Mar. 1, 2001

(65) Prior Publication Data

US 2002/0123764 A1 Sep. 5, 2002

(51) Int. Cl.[7] ................................................ A61B 17/00

(52) U.S. Cl. ....................................................... 606/190

(58) Field of Search ................................. 600/201, 184, 600/235; 606/96, 190, 191; D07/691; 30/324, 327

(56) References Cited

U.S. PATENT DOCUMENTS

| 379,553 A | * | 3/1888 | Allen | |
|---|---|---|---|---|
| 4,927,424 A | * | 5/1990 | McConnell et al. | 606/102 |
| 5,273,024 A | * | 12/1993 | Menon et al. | 128/898 |
| 5,902,231 A | * | 5/1999 | Foley et al. | 600/102 |

FOREIGN PATENT DOCUMENTS

EP 0552980 A1 * 1/1993 ........... A61B/17/00

* cited by examiner

*Primary Examiner*—David O. Reip
*Assistant Examiner*—D. Jacob Davis
(74) *Attorney, Agent, or Firm*—St. Onge Steward Johnston & Reens LLC

(57) ABSTRACT

A device for guiding a medical instrument is described, which comprises a guide tube, which has a longitudinal opening extending substantially from a distal end to a proximal end of the guide tube, wherein the guide tube comprises a rounded bottom and two parallel side walls so that the guide tube is about semi-circular in cross section. The device further comprises a handle connected to the guide tube in the region of the proximal end of the guide tube. The distal end of the guide tube is open, and the handle projects laterally from said guide tube.

5 Claims, 1 Drawing Sheet

DEVICE FOR GUIDING A MEDICAL INSTRUMENT

BACKGROUND OF THE INVENTION

The invention relates to a device for guiding a medical instrument, comprising a guide tube having a distal end and a proximal end, and having a longitudinal opening extending substantially from the distal end to the proximal end, wherein the guide tube has a rounded bottom and two parallel longitudinal side walls so that that guide tube is about semi-circular.

A device of the type mentioned before is known from EP 0 552 980 A1.

A device of the afore-mentioned type is used in the field of orthopaedics or in casualty surgery in order to facilitate the access for medical instruments to joints where surgical operations are to be carried out.

A particular field of application of such a device is the arthroscopy.

The device known from EP 0 552 980 A1 mentioned before comprises an elongated guide tube having a closed distal end, an open proximal end and a longitudinal opening or slot extending from a point near the closed distal end to a point near the open proximal end of the guide tube. The guide tube has a D-shaped cross section which extends substantially over the entire length of the tube. The flat part of the D-shaped cross section is situated along the edge of the longitudinal opening and the D-shaped cross section comprises a predetermined dimension for receiving and guiding an instrument axially inserted in the guide tube from the open end. Further, a handle is disposed at the proximal end of the guide tube of this known device, which extends in prolongation of the longitudinal axis of the guide tube.

This known device is particularly used for the treatment of the carpal-tunnel, in order to introduce instruments like an endoscope or a cutting instrument in the surgical area by means of the guide tube and to place them therein, accordingly.

A disadvantage of the known device is that the guide tube cannot be withdrawn from the surgical area when an instrument is inserted in the guide tube. Furthermore, the arrangement of the handle of the known device in axial prolongation of the guide tube is disadvantageous, because the handle represents an obstacle to the insertion of a medical instrument, for example an arthroscope, into the guide tube from the proximal end.

It is therefore an object of the present invention to improve a device of the type mentioned at the outset such that the disadvantages mentioned before are avoided, in particular the device can be easily removed from the surgical area after a medical instrument having been introduced by means of the guide tube.

SUMMARY OF THE INVENTION

According to the present invention, this object is achieved by a device for guiding a medical instrument, comprising:
- a guide tube having a distal end and a proximal end, and having a longitudinal slot extending substantially from said distal end to said proximal end, wherein said guide tube has a round bottom and two parallel longitudinal side walls, so that that guide tube is substantially half-circular in cross section; and
- a handle connected to said guide tube in the region of said proximal end of said guide tube, wherein said distal end of said guide tube is open, and wherein said handle laterally projects from said guide tube.

Since the distal end of the guide tube is open, the guide tube can be easily withdrawn from the surgical area along the instruments which have been introduced in the surgical area through the guide tube. While the instruments can remain in the surgical area, the device must not remain in the joint for maintaining the access as it is the case with conventional tube systems. Since the handle projects laterally from the guide tube, a medical instrument can be introduced in the surgical area along the guide tube from the proximal end thereof without any impediments. This has the advantage that the access of a medical instrument in a joint through soft tissues is possible without obstacles. In use of the device according to the present invention, the guide tube is advanced along an instrument previously introduced into the joint until the distal end of the guide tube can be seen through an endoscope. In the next step, the medical instrument previously introduced is withdrawn, whereafter another instrument can be advanced along the guide tube into the joint. The guide tube is subsequently withdrawn from the joint, whereas the instrument previously introduced can remain in the joint.

In a preferred embodiment, the proximal end of the guide tube is open.

In another preferred embodiment, the distal end of the guide tube is chamfered.

In another preferred embodiment, the handle projects from the guide tube substantially in a right angle.

In a still further embodiment, the handle projects from one of the side walls of the guide tube.

A preferred embodiment of the present invention will be described hereinafter with reference to the accompanying drawings, in which:

DETAILED DESCRIPTION OF A PREFERRED EMBODIMENT

Figure 1:
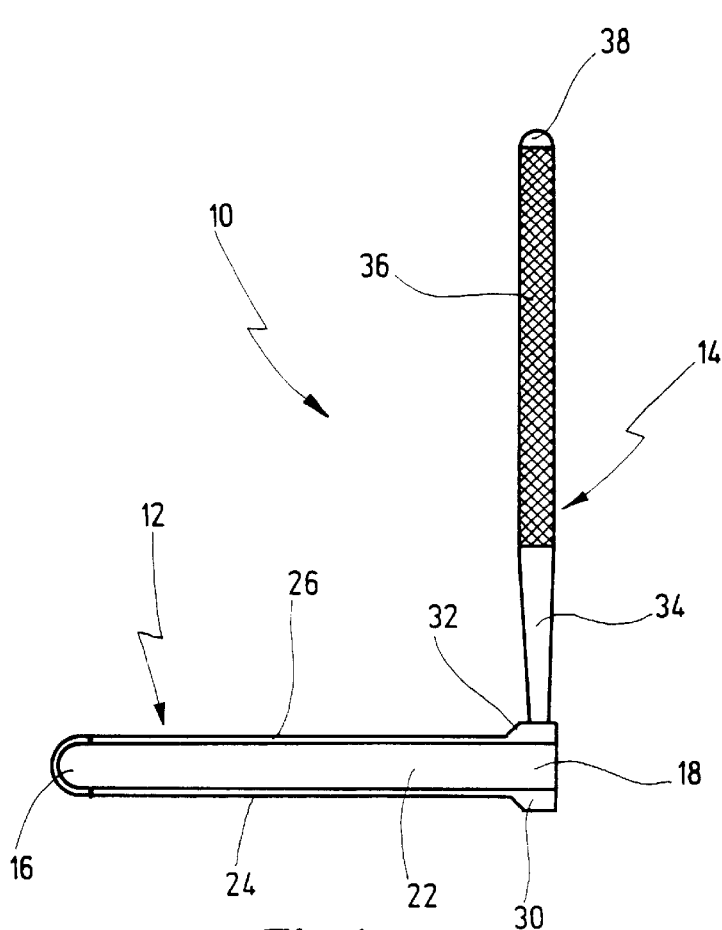
FIG. 1 is a top view of a device according to the present invention.
Figure 2:
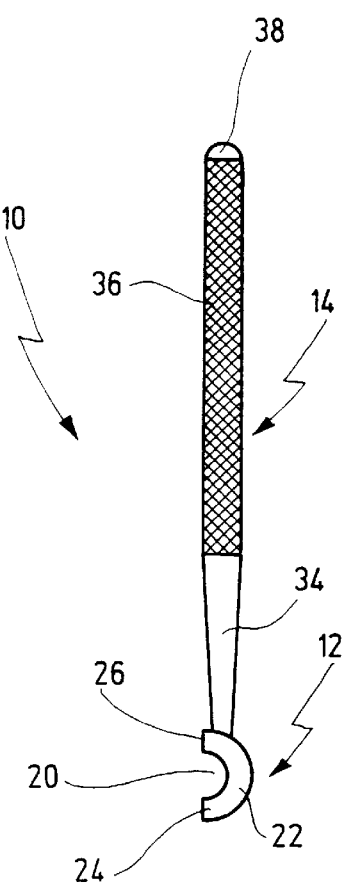
FIG. 2 is a view of the proximal end of the device in FIG. 1.
Figure 3:
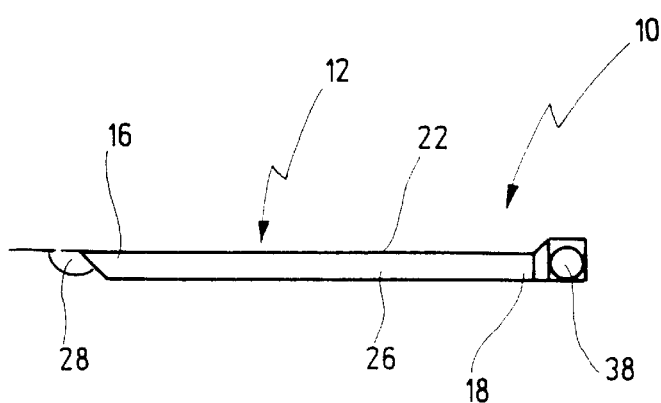
FIG. 3 is a side view of the device in FIG. 1 and 2, seen from the free end of the handle of the device.

In FIGS. 1 through 3, a device for guiding a medical instrument labeled with the general reference numeral 10 is depicted. The device 10 is used for introducing instruments into joints within the frame of minimal-invasive surgery, in particular in arthroscopy.

The device 10 comprises a guide tube 12 and a handle 14 which projects laterally from the guide tube 12.

The guide tube 12 comprises a longitudinal opening or slot 20 extending substantially from a distal end 16 to a proximal end 18 of the guide tube 12.

The guide tube 12 comprises a round bottom 22 and two parallel side walls 24 and 26. The guide tube 12, therefore, has an about D-shaped or C-shaped, about semi-circular cross section in its entirety.

The handle 14 is connected to the guide tube 12 at the proximal end 18 thereof.

The distal end 16 and the proximal end 18 of the guide tube 12 are configured as open ends. The guide tube 12, therefore, forms a guide channel forming an axially through-hole passage way in form of a "half pipe".

The distal end 16 of the guide tube 12 is chamfered. In the shown embodiment, an angle 28 amounts to 141° in FIG. 3, however other angles can be envisaged within the scope of the present invention.

The handle 14 projects from the guide tube 12 in an angle of about 90°. The handle 14 projects from one of the side walls 24, 26, and, in the shown embodiment, from the side wall 26.

The guide tube 12 is made from a round rod having a diameter of 12 mm. Other diameters can be chosen in order to make the guide tube with larger or lower radial dimensions. The length of the round rod is in the region between 70 and 90 mm.

In order to produce the guide tube 12, the round rod is turned off substantially over its entire length to a diameter of 8 mm. In a region 30 of the proximal end 18 of the guide tube 12, the round rod is left with a diameter of 12 mm over a length of 5 mm. A transition 32 from the 12 mm-diameter to the 8 mm-diameter is conically turned off. The round rod is subsequently hollowed by means of a 7 mm-drill. The hollow drilled round rod is subsequently separated in two halves. Then, the tip, i.e. the distal end 16 of the guide tube 12 is chamfered. The wall thickness of the guide tube 12 amounts to 0.5 mm when its production is complete.

The handle 14 is also made from a round rod having a diameter of 5 mm. This round rod conically tapers at an end 34 over a length of 27 mm from 5 mm to 3 mm. A remaining portion 36 of a length of 60 mm is knurled over its entire length and semi-spherically rounded at an end 38.

It is to be understood that all the afore-mentioned dimensions can be modified for different arthroscopic techniques.

The semi-open configuration of the guide tube 12 can be adapted in terms of its form (diameter of the guide tube 12) and in terms of the angle of the handle 14 with respect to the guide tube 12 to different joints.

With the device 10, the exchange of arthroscopic instruments in orthopaedics and in casualty surgery is facilitated. The advantage of the device 10 is that no supplementary device must remain in the joint during the surgical operation, because the guide tube 12 can be removed after the exchange of the instruments, whereas there is no limitation to the dimensions of the introduced instruments which is rendered possible by the semi-open configuration of the guide tube 12. Furthermore, the guide tube 12 allows an exchange of instruments without the instruments getting entangled in the soft tissue.

What is claimed is:

1. A device for guiding medical instruments, comprising:
    a guide tube having a distal end and a proximal end, and having a longitudinal opening extending substantially from said distal end to said proximal end, wherein said guide tube has a round bottom and two parallel longitudinal side walls, so that said guide tube is about semi-circular in cross section; and
    a handle connected to said guide tube in the region of said proximal end of said guide tube,
        wherein said distal end of said guide tube is open, and wherein said handle projects laterally from one of said side walls of said guide tube in a direction substantially perpendicular to said side walls.

2. The device of claim 1, wherein said proximal end of said guide tube is open.

3. The device of claim 1, wherein said distal end of said guide tube is chamfered.

4. The device of claim 1, wherein said handle projects from said guide tube substantially in a right angle.

5. The device for guiding medical instruments of claim 1 wherein a cross-section of said guide tube is substantially constant along substantially an entire length of said guide tube.

* * * * *